(12) United States Patent
Bui et al.

(10) Patent No.: US 9,278,060 B2
(45) Date of Patent: Mar. 8, 2016

(54) COMPOSITION CONTAINING A POLAR MODIFIED POLYMER

(75) Inventors: Hy Si Bui, Piscataway, NJ (US); Mohamed Kanji, Edison, NJ (US); Balanda Atis, Newark, NJ (US); Dhaval Patel, Edison, NJ (US); Susan Halpern, Paramus, NJ (US); Florentina Pavel, Hillsborough, NJ (US); Ella Rapoport, Morganville, NJ (US); Yoriko Kawaratani, Carteret, NJ (US); Michell Chen, Edison, NJ (US)

(73) Assignee: L'Oreal, Paris (FR)

( * ) Notice: Subject to any disclaimer, the term of this patent is extended or adjusted under 35 U.S.C. 154(b) by 540 days.

(21) Appl. No.: 12/825,003

(22) Filed: Jun. 28, 2010

(65) Prior Publication Data

US 2011/0020255 A1    Jan. 27, 2011

Related U.S. Application Data

(63) Continuation of application No. PCT/US2008/088434, filed on Dec. 29, 2008, and a continuation of application No. PCT/US2008/087567, filed on Dec. 19, 2008, and a continuation of application No. PCT/US2008/087314, filed on Dec. 18, 2008, and a continuation of application No. PCT/US2008/087062, filed on Dec. 17, 2008.

(60) Provisional application No. 61/017,411, filed on Dec. 28, 2007, provisional application No. 61/017,350, filed on Dec. 28, 2007, provisional application No. 61/017,396, filed on Dec. 28, 2007, provisional application No. 61/017,407, filed on Dec. 28, 2007.

(51) Int. Cl.
| | |
|---|---|
| *A61K 8/81* | (2006.01) |
| *A61K 8/898* | (2006.01) |
| *A61Q 1/02* | (2006.01) |
| *A61Q 1/06* | (2006.01) |
| *A61Q 1/10* | (2006.01) |

(52) U.S. Cl.
CPC ............. *A61K 8/8176* (2013.01); *A61K 8/8164* (2013.01); *A61K 8/898* (2013.01); *A61Q 1/02* (2013.01); *A61Q 1/06* (2013.01); *A61Q 1/10* (2013.01); *A61K 2800/31* (2013.01)

(58) Field of Classification Search
None
See application file for complete search history.

(56) References Cited

U.S. PATENT DOCUMENTS

| | | | |
|---|---|---|---|
| 6,126,929 A * | 10/2000 | Mougin | 424/70.7 |
| 7,186,766 B2 | 3/2007 | Harashina et al. | |
| 8,551,461 B2 | 10/2013 | Bui et al. | |
| 8,597,621 B2 | 12/2013 | Bui et al. | |
| 8,663,667 B2 | 3/2014 | Bui et al. | |
| 2003/0082218 A1 | 5/2003 | Ichinohe et al. | |
| 2004/0170586 A1 | 9/2004 | Ferrari et al. | |
| 2005/0220728 A1 | 10/2005 | Kanji et al. | |
| 2006/0084764 A1 * | 4/2006 | Hanna et al. | 525/242 |
| 2006/0104940 A1 | 5/2006 | Heinrichs et al. | |
| 2006/0110345 A1 * | 5/2006 | Lu et al. | 424/64 |
| 2006/0188459 A1 * | 8/2006 | Heinrichs et al. | 424/63 |
| 2007/0031361 A1 | 2/2007 | Herrmann et al. | |
| 2007/0212315 A1 | 9/2007 | Pastor et al. | |
| 2007/0256700 A1 | 11/2007 | Bodelin | |
| 2010/0330012 A1 | 12/2010 | Bui et al. | |
| 2010/0330015 A1 | 12/2010 | Bui et al. | |
| 2010/0330016 A1 | 12/2010 | Bui et al. | |
| 2010/0330017 A1 | 12/2010 | Bui et al. | |
| 2010/0330022 A1 | 12/2010 | Bui et al. | |
| 2010/0330024 A1 | 12/2010 | Bui et al. | |
| 2011/0020254 A1 | 1/2011 | Bui et al. | |
| 2011/0020256 A1 | 1/2011 | Bui et al. | |
| 2011/0020257 A1 | 1/2011 | Bui et al. | |
| 2011/0020259 A1 | 1/2011 | Bui et al. | |
| 2011/0020260 A1 | 1/2011 | Bui et al. | |
| 2011/0020261 A1 | 1/2011 | Bui et al. | |
| 2011/0021681 A1 | 1/2011 | Bui et al. | |
| 2011/0021683 A1 | 1/2011 | Bui et al. | |
| 2011/0038819 A1 | 2/2011 | Bui et al. | |
| 2011/0223123 A1 | 9/2011 | Bui et al. | |
| 2011/0280817 A1 | 11/2011 | Ramadan et al. | |
| 2011/0280818 A1 | 11/2011 | Kawaratani et al. | |
| 2011/0280819 A1 | 11/2011 | Bui et al. | |
| 2011/0280820 A1 | 11/2011 | Bui et al. | |
| 2011/0286949 A1 | 11/2011 | Bui et al. | |
| 2011/0286950 A1 | 11/2011 | Bui et al. | |
| 2011/0286951 A1 | 11/2011 | Bui et al. | |
| 2011/0286954 A1 | 11/2011 | Bui et al. | |
| 2011/0293550 A1 | 12/2011 | Bui et al. | |
| 2011/0311467 A1 | 12/2011 | Bui et al. | |
| 2012/0003169 A1 | 1/2012 | Bui et al. | |
| 2012/0004327 A1 | 1/2012 | Bui et al. | |
| 2012/0020907 A1 | 1/2012 | Bui et al. | |
| 2012/0107263 A1 | 5/2012 | Bui et al. | |
| 2012/0171140 A1 | 7/2012 | Bui et al. | |
| 2014/0004069 A1 | 1/2014 | Bui et al. | |
| 2014/0037565 A1 | 2/2014 | Bui et al. | |

FOREIGN PATENT DOCUMENTS

| | | | |
|---|---|---|---|
| DE | 102005026278 | * | 10/2005 |
| EP | 1 314 415 A1 | | 5/2003 |

OTHER PUBLICATIONS

U.S. Appl. No. 14/227,264, filed Mar. 27, 2014, Bui, et al. Communication pursuant to Article 94(3) EPC issued Jan. 2, 2014, in European Patent Application No. 08 867 867.7.
Supplementary Search Report issued Dec. 18, 2012 in European Patent Application No. 08867867.7-2108.
Extended European Search Report Issued Nov. 29, 2012 in Patent Application No. 08867867.7.
U.S. Appl. No. 14/147,726, filed Jan. 6, 2014, Bui, et al.
U.S. Appl. No. 14/241,361, filed Feb. 26, 2014, Motornov, et al.
U.S. Appl. No. 14/241,753, Feb. 27, 2014, Motornov, et al.

* cited by examiner

*Primary Examiner* — Jennifer A Berrios
(74) *Attorney, Agent, or Firm* — Oblon, McClelland, Maier & Neustadt, L.L.P

(57) ABSTRACT

The invention relates to a physiologically acceptable composition, especially a cosmetic composition, comprising at least one polar modified polymer, as well as to methods of using such compositions.

16 Claims, No Drawings

COMPOSITION CONTAINING A POLAR MODIFIED POLYMER

CROSS-REFERENCE TO RELATED APPLICATIONS

This application is a continuation of International Application No. PCT/US2008/088434, filed Dec. 29, 2008, which claims the benefit of U.S. Ser. No. 61/017,411, filed Dec. 28, 2007; and a continuation of International Application No. PCT/US2008/087567, filed Dec. 19, 2008, which claims the benefit of U.S. Ser. No. 61/017,350, filed Dec. 28, 2007; and a continuation of International Application No. PCT/US2008/087314, filed Dec. 18, 2008, which claims the benefit of U.S. Ser. No. 61/017,396, filed Dec. 28, 2007; and a continuation of International Application No. PCT/US2008/087062, filed Dec. 17, 2008, which claims the benefit of U.S. Ser. No. 61/017,407, filed Dec. 28, 2007, the entire contents of which are hereby incorporated by reference.

FIELD OF THE INVENTION

The present invention relates to compositions, for example, a cosmetic composition, comprising at least one polar modified polymer. Such compositions can possess improved properties and characteristics such as, for example, increased long wear and anti-smudging properties, improved shine/color characteristics and/or better texture and feel upon application.

DISCUSSION OF THE BACKGROUND

Many cosmetic compositions, including pigmented cosmetics such as foundations, concealers, lipsticks, and mascaras, and other cosmetic and sunscreen compositions, have been developed for longer wear and transfer resistance properties. This is generally accomplished by the use of compositions that form a film after application. Such compositions generally contain volatile solvents, which evaporate on contact with the skin or other keratinous tissue, leaving behind a layer comprising waxes and/or resins, pigments, fillers, and actives. However, these compositions tend to be uncomfortable for the wearer as the composition remains on the skin or other keratinous tissue as a brittle or non-flexible film. Such compositions may not be pliable or soft, and they may not be comfortable to wear. Furthermore, such compositions have a tendency to be tacky, resulting in poor application, spreadability and wear characteristics.

U.S. Pat. No. 6,492,455 discloses water-soluble reaction products of polyamines and C6 olefin/maleic anhydride copolymers. Because these compositions are water-soluble, addition of water to such reaction products renders the products unsuitable for applications requiring water-insolubility. For example, such reaction products are unsuitable for use as a solid carrier containing colorant (for example, industrial pigments) or active agents (for example, pharmaceuticals) because the reaction product breaks down upon exposure to water.

Thus, there remains a need for improved cosmetic compositions having improved cosmetic properties.

Accordingly, one aspect of the present invention is a care and/or makeup and/or treatment composition for keratinous material such as skin, hair, eyes, eyelashes, nails and/or lips, which is able to address or overcome at least one of the aforementioned problems with the prior art compositions.

SUMMARY OF THE INVENTION

The present invention relates to compositions, preferably cosmetic compositions, comprising at least one polar modified polymer. Preferably, the compositions further comprise at least one viscosity increasing agent.

The present invention also relates to colored cosmetic compositions comprising at least one coloring agent and at least one polar modified polymer. Preferably, the compositions further comprise at least one viscosity increasing agent. Such colored cosmetic compositions can be, for example, anhydrous lip compositions (for example, eye shadow, lipstick or liquid lip colors) or foundations.

The present invention further relates to colored cosmetic compositions comprising at least one polar modified polymer, at least one coloring agent and water. Preferably, the compositions further comprise at least one viscosity increasing agent and/or at least one volatile oil. Such water-containing colored cosmetic compositions are preferably foundations or mascaras, and are emulsions or dispersions.

The present invention also relates to methods of treating, caring for and/or making up keratinous material (for example, skin, eyes, eyelashes or lips) by applying compositions of the present invention to the keratinous material in an amount sufficient to treat, care for and/or make up the keratinous material.

The present invention further relates to covering or hiding skin defects associated with keratinous material (for example, skin or lips) by applying compositions of the present invention to the keratinous material in an amount sufficient to cover or hide such skin defects.

The present invention also relates to methods of enhancing the appearance of keratinous material (for example, skin, eyes, eyelashes, or lips) by applying compositions of the present invention to the keratinous material in an amount sufficient to enhance the appearance of the keratinous material.

The present invention further relates to compositions having improved cosmetic properties such as, for example, increased anti-smudging properties, increased long wear properties, improved shine/color characteristics and/or better texture or feel upon application.

The present invention also relates to methods of increasing both the anti-smudging properties and long wear properties of a composition comprising adding to a composition at least one polar modified polymer. Preferably, at least one viscosity increasing agent is also added to the compositions.

The present invention also relates to methods of improving the feel or texture properties of a composition upon application to a keratin material comprising adding to a composition (for example, a foundation) at least one polar modified polymer. Preferably, at least one viscosity increasing agent is also added to the compositions.

The present invention also relates to methods of making a composition comprising adding at least one polar modified polymer to a composition. Preferably, at least one viscosity increasing agent is also added to the compositions.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

"Film former" or "film forming agent" as used herein means a polymer or resin that leaves a film on the substrate to which it is applied, for example, after a solvent accompanying the film former has evaporated, absorbed into and/or dissipated on the substrate.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to human keratin material such as hair, skin or lips followed by rubbing a material, for example, a sheet of paper, against the hair, skin or lips after expiration of a certain amount of time following application, such as 2 minutes after application. Similarly, transfer resistance of a composition may be evaluated by the amount of product transferred from a wearer to any other substrate, such as transfer from the hair, skin or lips of an individual to a collar when putting on clothing after the expiration of a certain amount of time following application of the composition to the hair, skin or lips. The amount of composition transferred to the substrate (e.g., collar, or paper) may then be evaluated and compared. For example, a composition may be transfer resistant if a majority of the product is left on the wearer's hair, skin or lips. Further, the amount transferred may be compared with that transferred by other compositions, such as commercially available compositions. In a preferred embodiment of the present invention, little or no composition is transferred to the substrate from the hair, skin or lips.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to human hair, skin or lips and evaluating the color of the composition after an extended period of time. For example, the color of a composition may be evaluated immediately following application to hair, skin or lips and these characteristics may then be re-evaluated and compared after a certain amount of time. Further, these characteristics may be evaluated with respect to other compositions, such as commercially available compositions.

"Tackiness" as used herein refers to the adhesion between two substances. For example, the more tackiness there is between two substances, the more adhesion there is between the substances. To quantify "tackiness," it is useful to determine the "work of adhesion" as defined by IUPAC associated with the two substances. Generally speaking, the work of adhesion measures the amount of work necessary to separate two substances. Thus, the greater the work of adhesion associated with two substances, the greater the adhesion there is between the substances, meaning the greater the tackiness is between the two substances.

Work of adhesion and, thus, tackiness, can be quantified using acceptable techniques and methods generally used to measure adhesion, and is typically reported in units of force time (for example, gram seconds ("g s")). For example, the TA-XT2 from Stable Micro Systems, Ltd. can be used to determine adhesion following the procedures set forth in the TA-XT2 Application Study (ref: MATI/PO.25), revised January 2000, the entire contents of which are hereby incorporated by reference. According to this method, desirable values for work of adhesion for substantially non-tacky substances include less than about 0.5 g s, less than about 0.4 g s, less than about 0.3 g s and less than about 0.2 g s. As known in the art, other similar methods can be used on other similar analytical devices to determine adhesion.

"Waterproof" as used herein refers to the ability to repel water and permanence with respect to water. Waterproof properties may be evaluated by any method known in the art for evaluating such properties. For example, a mascara composition may be applied to false eyelashes, which may then be placed in water for a certain amount of time, such as, for example, 20 minutes. Upon expiration of the pre-ascertained amount of time, the false eyelashes may be removed from the water and passed over a material, such as, for example, a sheet of paper. The extent of residue left on the material may then be evaluated and compared with other compositions, such as, for example, commercially available compositions. Similarly, for example, a composition may be applied to skin, and the skin may be submerged in water for a certain amount of time. The amount of composition remaining on the skin after the pre-ascertained amount of time may then be evaluated and compared. For example, a composition may be waterproof if a majority of the product is left on the wearer, e.g., eyelashes, skin, etc. In a preferred embodiment of the present invention, little or no composition is transferred from the wearer.

The cosmetic compositions and methods of the present invention can comprise, consist of, or consist essentially of the essential elements and limitations of the invention described herein, as well as any additional or optional ingredients, components, or limitations described herein or otherwise useful in personal care compositions intended for topical application to hair.

The composition of the present invention may be in any form, either liquid or non-liquid (semi-solid, soft solid, solid, etc.). For example, it may be a paste, a solid, a gel, or a cream. It may be an emulsion, such as an oil-in-water or water-in-oil emulsion, a multiple emulsion, such as an oil-in-water-in-oil emulsion or a water-in-oil-in-water emulsion, or a solid, rigid or supple gel, including anhydrous gels. The composition can also be in a form chosen from a translucent anhydrous gel and a transparent anhydrous gel. The composition of the invention may, for example, comprise an external or continuous fatty phase. The composition may be anhydrous. The composition can also be a molded composition or cast as a stick or a dish. The composition in one embodiment is a solid such as a molded stick or a poured stick.

Depending on the intended application, such as a stick, hardness of the composition may also be considered. The hardness of a composition may, for example, be expressed in gramforce (gf). The composition of the present invention may, for example, have a hardness ranging from 20 gf to 2000 gf, such as from 20 gf to 900 gf, and further such as from 20 gf to 600 gf.

This hardness is measured in one of two ways. A first test for hardness is according to a method of penetrating a probe into the composition and in particular using a texture analyzer (for example TA-XT2i from Rheo) equipped with an ebonite cylinder of height 25 mm and diameter 8 mm. The hardness measurement is carried out at 20° C. at the center of 5 samples of the composition. The cylinder is introduced into each sample of composition at a pre-speed of 2 mm/s and then at a speed of 0.5 mm/s and finally at a post-speed of 2 mm/s, the total displacement being 1 mm. The recorded hardness value is that of the maximum peak observed. The measurement error is ±50 gf.

The second test for hardness is the "cheese wire" method, which involves cutting an 8.1 mm or preferably 12.7 mm in diameter stick composition and measuring its hardness at 20° C. using a DFGHS 2 tensile testing machine from Indelco- Chatillon Co. at a speed of 100 mm/minute. The hardness value from this method is expressed in grams as the shear force required to cut a stick under the above conditions. According to this method, the hardness of compositions according to the present invention which may be in stick form may, for example, range from 30 gf to 300 gf, such as from 30 gf to 250 gf, for a sample of 8.1 mm in diameter stick, and further such as from 30 gf to 200 gf, and also further such as from 30 gf to 120 gf for a sample of 12.7 mm in diameter stick.

The hardness of the composition of the present invention may be such that the compositions are self-supporting and can easily disintegrate to form a satisfactory deposit on keratin materials. In addition, this hardness may impart good impact strength to the inventive compositions, which may be molded or cast, for example, in stick or dish form.

The skilled artisan may choose to evaluate a composition using at least one of the tests for hardness outlined above based on the application envisaged and the hardness desired. If one obtains an acceptable hardness value, in view of the intended application, from at least one of these hardness tests, the composition falls within preferred embodiments of the invention.

As is evident, the hardness of the composition according to preferred embodiments of the invention may, for example, be such that the composition is advantageously self-supporting and can disintegrate easily to form a satisfactory deposit on keratin materials. In addition, with this hardness, the composition of the invention may have good impact strength.

According to preferred embodiments of the present invention, the composition in stick form may have the behavior of a deformable, flexible elastic solid, giving noteworthy elastic softness on application.

As defined herein, stability is tested by placing the composition in a controlled environment chamber for 8 weeks at 25° C. In this test, the physical condition of the sample is inspected as it is placed in the chamber. The sample is then inspected again at 24 hours, 3 days, 1 week, 2 weeks, 4 weeks and 8 weeks. At each inspection, the sample is examined for abnormalities in the composition such as phase separation if the composition is in the form of an emulsion, bending or leaning if the composition is in stick form, melting, or syneresis (or sweating). The stability is further tested by repeating the 8-week test at 25° C., 37° C., 45° C. and under freeze-thaw conditions. A composition is considered to lack stability if in any of these tests an abnormality that impedes functioning of the composition is observed. The skilled artisan will readily recognize an abnormality that impedes functioning of a composition based on the intended application.

Polar Modified Polymer

According to the present invention, compositions comprising at least one polar modified polymer are provided. "Polar modified polymer" as used herein refers to "oil-soluble polar modified polymers" and/or "oil-soluble high carbon polar modified polymers.

Oil-Soluble Polar Modified Polymer

According to the present invention, compositions comprising at least one oil-soluble polar modified polymer are provided. "Polar modified polymer" as used herein refers to a hydrophobic homopolymer or copolymer which has been modified with hydrophilic unit(s). "Oil-soluble" as used herein means that the polar modified polymer is soluble in oil.

Suitable monomers for the hydrophobic homopolymers and/or copolymers include, but are not limited to, cyclic, linear or branched, substituted or unsubstituted, C2-C20 compounds such as, for example, styrene, ethylene, propylene, isopropylene, butylene, isobutylene, pentene, isopentene, isoprene, hexene, isohexene, decene, isodecene, and octadecene, including all ranges and subranges therebetween. Preferably, the monomers are C2-C8 compounds, more preferably C2-C6 compounds, and most preferably C2-C4 compounds such as ethylene, propylene and butylene.

Suitable hydrophilic unit(s) include, but are not limited to, maleic anhydride, acrylates, alkyl acrylates such as, for example, methyl acrylate, ethyl acrylate, propyl acrylate, and butyl acrylate, and polyvinylpyrrolidone (PVP).

According to the present invention, the polar modified polymer is oil-soluble: that is, the polymer does not contain a sufficient amount of hydrophilic unit(s) to render the entire polymer water-soluble or oil-insoluble. According to preferred embodiments, the polar modified polymer contains the same amount of hydrophobic monomer as hydrophilic unit (1:1 ratio) or more hydrophobic monomer than hydrophilic unit. According to particularly preferred embodiments, the polar modified polymer contains 50% or less hydrophilic unit(s) (based on weight of the polymer), 40% or less hydrophilic unit(s), 30% or less hydrophilic unit(s), 20% or less hydrophilic unit(s), 10% or less hydrophilic unit(s), 5% or less hydrophilic unit(s), 4% or less hydrophilic unit(s), or 3% or less hydrophilic unit(s).

Preferably, the polar modified polymer has from about 0.5% to about 10% hydrophilic units, more preferably from about 1% to about 8% hydrophilic units by weight with respect to the weight of the polymer, including all ranges and subranges therebetween. Particularly preferred hydrophilically modified polymers are ethylene and/or propylene homopolymers and copolymers which have been modified with maleic anhydride units.

According to preferred embodiments of the present invention, the polar modified polymer is a wax. According to particularly preferred embodiments, the polar modified wax is made via metallocene catalysis, and includes polar groups or units as well as a hydrophobic backbone. Suitable modified waxes include those disclosed in U.S. patent application publication no. 20070031361, the entire contents of which is hereby incorporated by reference. Particularly preferred polar modified waxes are C2-C3 polar modified waxes.

In accordance with preferred embodiments of the present invention, the polar modified wax is based upon a homopolymer and/or copolymer wax of hydrophobic monomers and has a weight-average molecular weight Mw of less than or equal to 25 000 g/mol, preferably of 1000 to 22 000 g/mol and particularly preferably of 4000 to 20,000 g/mol, a number-average molecular weight Mn of less than or equal to 15 000 g/mol, preferably of 500 to 12 000 g/mol and particularly preferably of 1000 to 5000 g/mol, a molar mass distribution Mw/Mn in the range from 1.5 to 10, preferably from 1.5 to 5, particularly preferably from 1.5 to 3 and especially preferably from 2 to 2.5, which have been obtained by metallocene catalysis. Also, the polar modified wax preferably has a melting point above 75° C., more preferably above 90° C. such as, for example, a melting point between 90° C. and 160° C., preferably between 100° C. and 150° C., including all ranges and subranges therebetween.

In the case of a copolymer wax, it is preferable to have, based on the total weight of the copolymer backbone, 0.1 to 30% by weight of structural units originating from the one monomer and 70.0 to 99.9% by weight of structural units originating from the other monomer. Such homopolymer and copolymer waxes can be made, for example, by the process described in EP 571 882, the entire contents of which is hereby incorporated by reference, using the metallocene catalysts specified therein. Suitable preparation processes include, for example, suspension polymerization, solution polymerization and gas-phase polymerization of olefins in the presence of metallocene catalysts, with polymerization in the monomers also being possible.

Polar modified waxes can be produced in a known manner from the hompopolymers and copolymers described above by oxidation with oxygen-containing gases, for example air, or by graft reaction with polar monomers, for example maleic acid or acrylic acid or derivatives of these acids. The polar modification of metallocene polyolefin waxes by oxidation with air is described, for example, in EP 0 890 583 A1, and the modification by grafting is described, for example, in U.S. Pat. No. 5,998,547, the entire contents of both of which are hereby incorporated by reference in their entirety.

Acceptable polar modified waxes include, but are not limited to, homopolymers and/or copolymers of ethylene and/or propylene groups which have been modified with hydrophilic units such as, for example, maleic anhydride, acrylate, methacrylate, polyvinylpyrrolidone (PVP), etc. Preferably, the C2-C3 wax has from about 0.5% to about 10% hydrophilic units, more preferably from about 1% to about 8% hydrophilic units by weight with respect to the weight of the wax, including all ranges and subranges therebetween. Particularly preferred hydrophilically modified waxes are ethylene and/or propylene homopolymers and copolymers which have been modified with maleic anhydride units.

Particularly preferred C2-C3 polar modified waxes for use in the present invention are polypropylene and/or polyethylene-maleic anhydride modified waxes ("PEMA," "PPMA," "PEPPMA") commercially available from Clariant under the trade name LICOCARE or LICOCENE, Specific examples of such waxes include products marketed by Clariant under the LicoCare name having designations such as PP207.

Other suitable polar modified polymers include, but are not limited to A-C 573 A (ETHYLENE-MALEIC ANHYDRIDE COPOLYMER; Drop Point, Mettler: 106° C.) from Honeywell, A-C 596 A (PROPYLENE-MALEIC ANHYDRIDE COPOLYMER; Drop Point, Mettler: 143° C.) from Honeywell, A-C 597 (PROPYLENE-MALEIC ANHYDRIDE COPOLYMER; Drop Point, Mettler: 141° C.) from Honeywell, ZeMac® copolymers (from VERTELLUS) which are 1:1 copolymers of ethylene and maleic anhydride, polyisobutylene-maleic anhydride sold under the trade name ISOBAM (from Kuraray), polyisoprene-graft-maleic anhydride sold by Sigma Aldrich, poly(maleic anhydride-octadecene) sold by Chevron Philips Chemical Co., poly(ethylene-co-butyl acrylate-co-maleic anhydride) sold under the trade name of Lotader (e.g. 2210, 3210, 4210, and 3410 grades) by Arkema, copolymers in which the butyl acrylate is replaced by other alkyl acrylates (including methyl acrylate [grades 3430, 4404, and 4503] and ethyl acrylate [grades 6200, 8200, 3300, TX 8030, 7500, 5500, 4700, and 4720) also sold by Arkema under the Lotader name, and isobutylene maleic anhydride copolymer sold under the name ACO-5013 by ISP.

According to other embodiments of the present invention, the polar modified polymer is not a wax. In accordance with these embodiments of the present invention, the polar modified polymer is based upon a homopolymer and/or copolymer of hydrophobic monomer(s) and has a weight-average molecular weight Mw of less than or equal to 1,000,000 g/mol, preferably of 1000 to 250,000 g/mol and particularly preferably of 5,000 to 50,000 g/mol, including all ranges and subranges therebetween.

In accordance with these embodiments, the polar modified polymer can be of any form typically associated with polymers such as, for example, block copolymer, a grafted copolymer or an alternating copolymer. For example, the polar modified polymer can contain a hydrophobic backbone (such as polypropylene and/or polyethylene) onto which hydrophilic groups (such as maleic anhydride) have been attached by any means including, for example, grafting. The attached groups can have any orientation (for example, atactic, isotactic or syndiotactic along the backbone).

Preferably, the oil soluble polar modified polymer(s) represent from about 0.1% to about 30% of the total weight of the composition, more preferably from about 0.5% to about 20% of the total weight of the composition, and most preferably from about 1% to about 15%, including all ranges and subranges therebetween such as, for example, about 5% to about 15% and about 10% to about 20%.

Oil-Soluble High Carbon Polar Modified Polymer

According to the present invention, compositions comprising at least one oil-soluble high carbon polar modified polymer are provided. "Polar modified polymer" as used herein refers to a hydrophobic homopolymer or copolymer which has been modified with hydrophilic unit(s). "Oil-soluble" as used herein means that the polar modified polymer is soluble in oil. "High carbon" means more than 20 carbon atoms.

Suitable monomers for the hydrophobic homopolymers and/or copolymers include, but are not limited to, cyclic, linear or branched, substituted or unsubstituted, C22-C40 compounds such as, C22-C28 compounds, C24-C26 compounds, C26-C28 compounds, and C30-C38 compounds, including all ranges and subranges therebetween. Preferably, the monomers are C24-26 compounds, C26-C28 compounds or C30-C38 compounds.

Suitable hydrophilic unit(s) include, but are not limited to, maleic anhydride, acrylates, alkyl acrylates such as, for example, methyl acrylate, ethyl acrylate, propyl acrylate, and butyl acrylate, and polyvinylpyrrolidone (PVP).

According to preferred embodiments, the oil-soluble high carbon polar modified polymer is a wax. Also preferably, the oil-soluble high carbon polar modified polymer wax has one or more of the following properties:

a weight-average molecular weight Mw of less than or equal to 30 000 g/mol, preferably of 500 to 10 000 g/mol and particularly preferably of 1000 to 5,000 g/mol, including all ranges and subranges therebetween;

a number-average molecular weight Mn of less than or equal to 15 000 g/mol, preferably of 500 to 12 000 g/mol and particularly preferably of 1000 to 5000 g/mol, including all ranges and subranges therebetween;

a molar mass distribution Mw/Mn in the range from 1.5 to 10, preferably from 1.5 to 5, particularly preferably from 1.5 to 3 and especially preferably from 2 to 2.5, including all ranges and subranges therebetween; and/or a crystallinity of 8% to 60%, preferably 9% to 40%, and more preferably 10% to 30%, including all ranges and subranges therebetween, as determined by differential scanning calorimetry.

According to preferred embodiments relating to a copolymer wax, it is preferable to have, based on the total weight of the copolymer backbone, 0.1 to 30% by weight of structural units originating from the one monomer and 70.0 to 99.9% by weight of structural units originating from the other monomer.

Waxes of the present invention can be based upon homopolymers or copolymers made, for example, by the process described in EP 571 882, the entire contents of which is hereby incorporated by reference. Suitable preparation processes include, for example, suspension polymerization, solution polymerization and gas-phase polymerization of olefins in the presence of catalysts, with polymerization in the monomers also being possible.

Oil-soluble high carbon polar modified polymer wax can be produced in a known manner from the hompopolymers and copolymers described above by oxidation with oxygen-containing gases, for example air, or by graft reaction with polar monomers, for example maleic acid or acrylic acid or derivatives of these acids. The polar modification of polyolefin waxes by oxidation with air is described, for example, in EP 0 890 583 A1, and the modification by grafting is described, for example, in U.S. Pat. No. 5,998,547, the entire contents of both of which are hereby incorporated by reference in their entirety.

Acceptable oil-soluble high carbon polar modified polymer waxes include, but are not limited to, homopolymers and/or copolymers of C24, C25 and/or C26 groups, copolymers C26, C27 and/or C28 groups, or copolymers of C30-C38 groups, which have been modified with hydrophilic units such as, for example, maleic anhydride, acrylate, methacrylate, polyvinylpyrrolidone (PVP), etc. Preferably, the oil-soluble high carbon polar modified polymer wax has from about 5% to about 30% hydrophilic units, more preferably from about 10% to about 25% hydrophilic units by weight with respect to the weight of the wax, including all ranges and subranges therebetween. Particularly preferred hydrophilically modified waxes are C26, C27 and/or C28 homopolymers and copolymers which have been modified with maleic anhydride units.

Particularly preferred oil-soluble high carbon polar modified polymer waxes for use in the present invention are C26-C28 alpha olefin maleic acid anhydride copolymer waxes commercially available from Clariant under the trade name LICOCARE or LICOCENE. Specific examples of such waxes include products marketed by Clariant under the Lico-Care name having designations such as CM 401, which is a maleic anhydride modified wax having a Mw of 2025 and a crystallinity of 11%, C30-C38 olefin/isopropylmaleate/maleic anhydride copolymer sold by Baker Hughes under the name Performa® V 1608, and C24-C26 alpha olefin acrylate copolymer wax commercially available from Clariant under the trade name LICOCARE CA301 LP3346 based on a polar backbone with C24-26 side chains with alternating ester and carboxylic acid groups.

According to other embodiments of the present invention, the polar modified polymer is not a wax. In accordance with these embodiments of the present invention, the polar modified polymer is based upon a homopolymer and/or copolymer of hydrophobic monomer(s) and has a weight-average molecular weight Mw of less than or equal to 1,000,000 g/mol, preferably of 1000 to 250,000 g/mol and particularly preferably of 5,000 to 50,000 g/mol, including all ranges and subranges therebetween.

In accordance with these embodiments, the polar modified polymer can be of any form typically associated with polymers such as, for example, block copolymer, a grafted copolymer or an alternating copolymer. For example, the polar modified polymer can contain a hydrophobic backbone (such as polypropylene and/or polyethylene) onto which hydrophilic groups (such as maleic anhydride) have been attached by any means including, for example, grafting. The attached groups can have any orientation (for example, atactic, isotactic or syndiotactic along the backbone).

Preferably, the oil-soluble high carbon polar modified polymer(s) represent from about 0.1% to about 30% of the total weight of the composition, more preferably from about 0.5% to about 20% of the total weight of the composition, and most preferably from about 1% to about 15%, including all ranges and subranges therebetween such as, for example, about 5% to about 15% and about 10% to about 20%.

Viscosity Increasing Agents

According to preferred embodiments, the compositions of the present invention further comprise at least one viscosity increasing agent. Any agent capable of increasing the viscosity of a composition is suitable for use as a viscosity increasing agent in accordance with the present invention.

Waxes are suitable viscosity increasing agents. For the purposes of the present invention, a typical wax is a lipophilic fatty compound that is solid at room temperature (25° C.) and atmospheric pressure (760 mmHg, i.e. 101 KPa), which undergoes a reversible solid/liquid change of state, having a melting point of greater than 40° C. and further such as greater than 55° C. and which may be up to 200° C. By bringing the wax to its melting point, it is possible to make it miscible with oils and to form a microscopically homogeneous mixture, but on returning the temperature of the mixture to room temperature, recrystallization of the wax in the oils of the mixture is obtained. It is this recrystallization in the mixture which is responsible for the reduction in the gloss of the mixture.

For the purposes of the invention, the waxes are those generally used in cosmetics and dermatology; they are, for example, of natural origin, for instance beeswax, ozokerite, carnauba wax, candelilla wax, ouricury wax, Japan wax, cork fiber wax, sugar cane wax, paraffin wax, lignite wax, microcrystalline waxes, lanolin wax, montan wax, ozokerites and hydrogenated oils such as hydrogenated jojoba oil as well as waxes of synthetic origin, for instance polyethylene waxes derived from the polymerization of ethylene, waxes obtained by Fischer-Tropsch synthesis, fatty acid esters and glycerides that are solid at 40° C., for example, at above 55° C., fatty alcohol waxes such as those sold by Baker Petrolite under the Performacol name (Performacol 350, 425 and 550) including C30-050 alcohols, silicone waxes such as alkyl- and alkoxy-poly(di)methylsiloxanes and/or poly(di)methyl-siloxane esters that are solid at 40° C., for example, at above 55° C.

According to the invention, the melting point values correspond to the melting peak measured by the "Differential Scanning Calorimetry" method with a temperature rise of 5 or 10° C./min.

According to particularly preferred embodiments of the present invention, compositions comprising at least one low melting point polyolefin wax are provided. As used herein, the phrase "low melting point" refers to polyolefin waxes having a melting point of less than 80° C., preferably less than 75° C., most preferably between about 50° C. and 75° C., including all ranges and subranges therebetween.

Preferably, the polyolefin wax used in accordance with the present invention results from the polymerization, and in particular from the homopolymerization, of an alpha-olefin corresponding to the general formula: R—CH=CH$_2$, in which R denotes an alkyl radical having at least 10 carbon atoms, preferably from 10 to 50 carbon atoms and more preferably from 25 to 50 carbon atoms. R is preferably a linear alkyl radical. According to the invention, the term "homopolymerization of an alpha-olefin" is understood to mean the polymerization of monomers composed essentially of an alpha-olefin or a mixture of alpha-olefins as defined above. Such waxes also include hyperbranched polyolefin waxes such as Performa V 343 produced by New Phase Technologies.

Preferably, the polyolefin wax has a number-average molecular weight ranging from 400 to 3000, more preferably from 2000 to 3000, and better still from 2500 to 2700. Suitable examples of such polyolefins are disclosed in U.S. Pat. Nos. 6,641,821, 6,464,967, 4,060,569, and 4,239,546, the disclosures of all of which are specifically incorporated by reference herein. Commercial examples of such waxes are sold in particular under the name of "Performa V (Reg) 103", "Performa (Reg) 253" and "Performa V (Reg) 260" by New Phase Technologies.

Other suitable viscosity increasing agents include elastomers. For example, suitable viscosity increasing agents include elastomeric compounds such as those sold or made under the names KSG6 from Shin-Etsu, Trefil E-505C or Trefil E-506C from Dow-Corning, Gransil from Grant Industries (SR-CYC, SR DMF10, SR-DC556) or those marketed in the form of preconstituted gels (KSG15, KSG17, KSG16, KSG18, KSG21 from Shin-Etsu, Gransil SR 5CYC gel, Gransil SR DMF 10 gel, Gransil SR DC556 gel, SF 1204 and JK 113 from General Electric or emulsifying elastomers such as those sold under the names of KSG-210, KSG-30, KSG-31, KSG-32, KSG-33, KSG-40, KSG 41, KSG-42, KSG-43 and KSG-44 from Shin-Etsu.

Other suitable viscosity increasing agents include polysilicone-polyamide copolymers such as those disclosed in U.S. patent application publication no. 2004/0170586, the entire contents of which is hereby incorporated by reference in its entirety. For example, a suitable polysilicone-polyamide copolymer comprises at least one moiety of formula (III) or (IV):

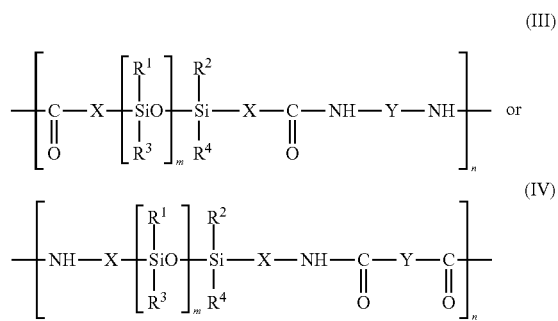

in which
1) $R^1$, $R^2$, $R^3$ and $R^4$, which may be identical or different, represent a group chosen from:

linear, branched or cyclic, saturated or unsaturated, $C_1$ to $C_{40}$ hydrocarbon-based groups, possibly containing in their chain one or more oxygen, sulphur and/or nitrogen atoms, and possibly being partially or totally substituted with fluorine atoms, $C_6$ to $C_{10}$ aryl groups, optionally substituted with one or more $C_1$ to $C_4$ alkyl groups, polyorganosiloxane chains possibly containing one or more oxygen, sulphur and/or nitrogen atoms;

2) the groups X, which may be identical or different, represent a linear or branched $C_1$ to $C_{30}$ alkylenediyl group, possibly containing in its chain one or more oxygen and/or nitrogen atoms;

3) Y is a saturated or unsaturated, $C_1$ to $C_{50}$ linear or branched divalent alkylene, arylene, cycloalkylene, alkylarylene or arylalkylene group, possibly comprising one or more oxygen, sulphur and/or nitrogen atoms, and/or bearing as substituent one of the following atoms or groups of atoms:

fluorine, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl groups, $C_1$ to $C_3$ hydroxyalkyl and $C_1$ to $C_6$ aminoalkyl, or 4) Y represents a group corresponding to the formula:

in which
T represents a linear or branched, saturated or unsaturated, $C_3$ to $C_{24}$ trivalent or tetravalent hydrocarbon-based group optionally substituted with a polyorganosiloxane chain, and possibly containing one or more atoms chosen from O, N and S, or T represents a trivalent atom chosen from N, P and Al, and
$R^5$ represents a linear or branched $C_1$ to $C_{50}$ alkyl group or a polyorganosiloxane chain, possibly comprising one or more ester, amide, urethane, thiocarbamate, urea, thiourea and/or sulphonamide groups, which may possibly be linked to another chain of the polymer;
5) n is an integer ranging from 2 to 500, and m is an integer ranging from 1 to 1000. A specific example of such copolymers are nylon 611/dimethicone copolymers marketed by Dow Corning.

Other suitable viscosity increasing agents include clays such as, for example, hectorites modified with an ammonium chloride of a $C_{10}$ to $C_{22}$ fatty acid, such as hectorite modified with distearyldimethylammonium chloride, also known as quaternium-18 bentonite, such as the products sold or made under the names Bentone 34 by the company Rheox, Claytone XL, Claytone 34 and Claytone 40 sold or made by the company Southern Clay, the modified clays known under the name quaternium-18 benzalkonium bentonites and sold or made under the names Claytone HT, Claytone GR and Claytone PS by the company Southern Clay, the clays modified with stearyldimethylbenzoylammonium chloride, known as steralkonium bentonites, such as the products sold or made under the names Claytone APA and Claytone AF by the company Southern Clay, and Baragel 24 sold or made by the company Rheox.

Other suitable viscosity increasing agents include silica, such as fumed silica. The fumed silica may have a particle size, which may be nanometric to micrometric, for example ranging from about 5 nm to 200 nm.

The fumed silicas may be obtained by high-temperature hydrolysis of a volatile silicon compound in a hydrogen-oxygen flame, producing a finely divided silica. This process makes it possible to obtain hydrophilic silicas that have a large number of silanol groups at their surface. Such hydrophilic silicas are sold or made, for example, under the names "Aerosil 130®", "Aerosil 200®", "Aerosil 255®", "Aerosil 300®" and "Aerosil 380®" by the company Degussa, and "CAB-O-SIL HS-55®", "CAB-O-SIL EH-5®", "CAB-O-SIL LM-130®", "CAB-O-SIL MS-55®" and "CAB-O-SIL M-5®" by the company Cabot.

It is thus possible to chemically modify the surface of the hydrophilic silica by chemical reaction, producing a reduction in the number of silanol groups. The silanol groups can be replaced, for example, with hydrophobic groups: this then gives a hydrophobic silica. The hydrophobic groups may be (a) trimethylsiloxyl groups, which are obtained in particular by treating fumed silica in the presence of hexamethyldisilazane. Silicas thus treated are known as "silica silylate" according to the CTFA (6th edition, 1995). They are sold or made, for example, under the references "Aerosil R812®" by the company Degussa and "CAB-O-SIL TS-530®" by the company Cabot; (b) dimethylsilyloxyl or polydimethylsiloxane groups, which are obtained in particular by treating fumed silica in the presence of polydimethylsiloxane or dimethyldichlorosilane. Silicas thus treated are known as "silica dimethyl silylate" according to the CTFA (6th edition, 1995). They are sold or made, for example, under the references "Aerosil R972®" and "Aerosil R974®" by the company Degussa, and "CAB-O-SIL TS-610®" and "CAB-O-SIL TS-720®" by the company Cabot; and (c) groups derived from reacting fumed silica with silane alkoxides or siloxanes. These treated silicas are, for example, the products sold or made under the reference "Aerosil R805®" by the company Degussa.

Using hydrophobic silicas, such as fumed silica, makes can help in obtaining a translucent or even transparent composition, in particular in the form of a stick, which does not exude, in the absence of opacifying particles such as waxes, fillers and pigments (including nacres).

Other suitable viscosity agents include liposoluble or lipodispersible rheological modifying agents such as, for example, PVP.

However, according to some embodiments of the present invention, the compositions contain so little of the viscosity increasing agents discuss above that the presence of such agents does not affect the cosmetic properties of the composition. Preferably, in such embodiments the compositions are substantially free of such viscosity increasing agents (i.e., contain less than about 1% viscosity increasing agents), essentially free of such viscosity increasing agents (i.e., contain less than about 0.5% viscosity increasing agents) or free of such viscosity increasing agents (i.e., contain less than about 0.1% viscosity increasing agents).

According to other preferred embodiments, the compositions contain so little elastomer and/or wax that the presence of such elastomers and/or waxes does not affect the cosmetic properties of the composition. Preferably, in such embodiments the compositions are substantially free of such elastomers and/or waxes (i.e., contain less than about 0.5% elastomers and/or waxes), essentially free of such elastomers and/or waxes (i.e., contain less than about 0.25% elastomers and/or waxes) or free of such elastomers and/or waxes (i.e., contain less than about 0.1% elastomers and/or waxes).

Preferably, the viscosity increasing agent, when present, is present in an amount sufficient to increase viscosity of the composition. Preferably, the viscosity increasing agent(s) represent from about 0.01% to about 40% of the total weight of the composition, more preferably from about 0.1 to about 30%, more preferably from about 0.5% to about 20%, more preferably from about 1% to about 15%, including all ranges and subranges therebetween such as, for example, about 5% to about 15% and about 10% to about 20%.

Volatile Oil

According to particularly preferred embodiments of the present invention, compositions optionally further comprising at least one volatile oil are provided. Preferably, the at least one volatile oil is a silicone volatile oil, a hydrocarbon volatile oil, or a mixture thereof.

According to preferred embodiments, the composition may contain one or more volatile silicone oils. Examples of such volatile silicone oils include linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
| --- | --- | --- |
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |
| PDMS DC 200 (5 cSt) from Dow Corning | 134 | 5 |
| PDMS DC 200 (3 St) from Dow Corning | 102 | 3 |

Further, a volatile linear silicone oil may be employed in the compositions of the present invention. Suitable volatile linear silicone oils include those described in U.S. Pat. No. 6,338,839 and WO03/042221, the contents of which are incorporated herein by reference. In one embodiment the volatile linear silicone oil is decamethyltetrasiloxane. In another embodiment, the decamethyltetrasiloxane is further combined with another solvent that is more volatile than decamethyltetrasiloxane.

According to other preferred embodiments, the composition may contain one or more non-silicone volatile oils and may be selected from volatile hydrocarbon oils, volatile esters and volatile ethers. Examples of such volatile non-silicone oils include, but are not limited to, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of Isopar or Permethyl, the $C_8$ to $C_{16}$ branched esters such as isohexyl or isodecyl neopentanoate and their mixtures. Preferably, the volatile non-silicone oils have a flash point of at least 40° C.

Non-limiting examples of volatile non-silicone volatile oils are given in Table 2 below.

TABLE 2

| Compound | Flash Point (° C.) |
| --- | --- |
| Isododecane | 43 |
| Isohexadecane | 102 |
| Isodecyl Neopentanoate | 118 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

The volatility of the solvents/oils can be determined using the evaporation speed as set forth in U.S. Pat. No. 6,338,839.

Preferably, the volatile oil(s), when present, represent from about 5% to about 90% of the total weight of the composition, more preferably from about 10% to about 80% of the total weight of the composition, and most preferably from about 20% to about 75%, including all ranges and subranges therebetween.

Coloring Agents

According to particularly preferred embodiments of the present invention, compositions optionally further comprising at least one at least one coloring agent are provided. Preferably, such colored compositions are cosmetic compositions such as, for example, lip compositions (for example, lipstick or liquid lip colors), mascaras, nail polish or foundations.

According to this embodiment, the at least one coloring agent is preferably chosen from pigments, dyes, such as liposoluble dyes, nacreous pigments, and pearling agents.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow. The liposoluble dyes, when present, generally have a concentration ranging up to 20% by weight of the total weight of the composition, such as from 0.0001% to 6%.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, be present in the composition in a concentration ranging up to 50% by weight of the total weight of the composition, such as from 0.1% to 20%, preferably from 0.1% to 15%, including all ranges and subranges therebetween.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum.

If present, the pigments may be present in the composition in a concentration ranging up to 50% by weight of the total weight of the composition, such as from 0.5% to 40%, and further such as from 2% to 30%, including all ranges and subranges therebetween. In the case of certain products, the pigments, including nacreous pigments, may, for example, represent up to 50% by weight of the composition.

Film Forming Agents

According to particularly preferred embodiments of the present invention, compositions optionally further comprising at least one at least one film forming agent (film former) are provided. Acceptable film forming agents are known in the art and include, but are not limited to, those disclosed in U.S. patent application publication no. 2004/0170586, the entire contents of which is hereby incorporated by reference. Non-limiting representative examples of such film forming agents include silicone resins such as, for example, MQ resins (for example, trimethylsiloxysilicates), T-propyl silsesquioxanes and MK resins (for example, polymethylsilsesquioxanes), silicone esters such as those disclosed in U.S. Pat. Nos. 6,045,782, 5,334,737, and 4,725,658, the disclosures of which are hereby incorporated by reference, polymers comprising a backbone chosen from vinyl polymers, methacrylic polymers, and acrylic polymers and at least one chain chosen from pendant siloxane groups and pendant fluorochemical groups such as those disclosed in U.S. Pat. Nos. 5,209,924, 4,693,935, 4,981,903, 4,981,902, and 4,972,037, and WO 01/32737, the disclosures of which are hereby incorporated by reference, polymers such as those described in U.S. Pat. No. 5,468,477, the disclosure of which is hereby incorporated by reference (a non-limiting example of such polymers is poly(dimethylsiloxane)-g-poly(isobutyl methacrylate), which is commercially available from 3M Company under the tradename VS 70 IBM).

According to preferred embodiments, the film former, when present, is present in the composition in an amount ranging from 0.1% to 30% by weight relative to the total weight of the composition. Preferably, the film former is present in an amount ranging from 0.5% to 20% by weight relative to the total weight of the composition, and more preferably from 2% to 15%, including all ranges and subranges therebetween. One of ordinary skill in the art will recognize that the film former of the present invention may be commercially available, and may come from suppliers in the form of a dilute solution. The amounts of the film former disclosed herein therefore reflect the weight percent of active material.

According to particularly preferred embodiments, when a film forming agent is present, the combined amount of the amount of polar modified polymer and the film forming agent is 30-50% by weight of the entire weight of the composition.

According to preferred embodiments of the present invention, the compositions of the present invention are anhydrous. By "anhydrous," it is meant that the composition contains substantially no water (that is, less than about 0.5% by weight of the composition of water).

According to preferred embodiments, an anhydrous composition, preferably a mascara, is provided. According to such embodiments, it is preferred to prepare such compositions by solubilizing the polar modified polymer in an oil (such as, for example, a volatile oil such as isododecane, an ester such as isononyl isononanoate, or hydrogenated polydecene such as that sold under the trade name PureSyn 2) under high shear.

According to particularly preferred anhydrous embodiments, low Mw polar modified polymers can be used. For example, polar modified polymers having a Mw of less than 10,000 preferably less than 7,000, and most preferably less than about 3,000 (for example, 2,025) can be used.

According to other preferred embodiments, the compositions of the present invention further comprise water. In this embodiment, water is preferably present in an amount ranging from about 0.6 to about 70%, preferably from about 3.0 to 60%, and more preferably from about 5 to about 50% relative to the total weight of the composition. Preferably, such water-containing cosmetic compositions are lip compositions (for example, lipstick or liquid lip colors), foundations or mascaras, and are emulsions or dispersions.

According to particularly preferred embodiments, the compositions of the present invention are in the form of an emulsion. Suitable emulsion forms include but are not limited to oil-in-water, water-in-oil, oil-in-water-in-oil, water-in-oil-in-water and nanoemulsions (emulsions whose oil globules are of very fine particle size, that is to say that they have a number-average size of less than about 100 nanometers (nm)). Emulsions contain at least one oil phase and at least one aqueous phase. Typically speaking, emulsions contain surfactants or surfactant-like materials which provide stability to the emulsions and inhibit de-phasing of the emulsions.

According to preferred embodiments, emulsion compositions can be easily removed from the keratin material to which they have been applied (for example, they are washable).

One particularly preferred embodiment of the present invention is a composition for application to keratin materials which is an emulsion but which is substantially free of surfactant (that is, less than 4% of surfactant) or essentially free of surfactant (that is, less than 2% surfactant). According to a particularly preferred embodiment, the emulsion contains only one surfactant.

If surfactants are present, preferred surfactants include O/W surfactants such as those sold under the names Tween 20, Inutec and Amphisol K.

Another particularly preferred embodiment of the present invention is a composition for application to keratin materials (hair or eyelashes) which is an emulsion but which is substantially free of TEA-stearate (that is, less than 0.25% of TEA-stearate) or free of TEA Stearate (that is, less than 0.05% TEA-stearate).

Additional Additives

The composition of the invention can also comprise any additive usually used in the field under consideration. For example, dispersants such as poly(12-hydroxystearic acid), antioxidants, essential oils, sunscreens, preserving agents, fragrances, fillers, neutralizing agents, cosmetic and dermatological active agents such as, for example, emollients, moisturizers, vitamins, essential fatty acids, surfactants, pasty compounds and mixtures thereof can be added. A non-exhaustive listing of such ingredients can be found in U.S. patent application publication no. 2004/0170586, the entire contents of which is hereby incorporated by reference. Further examples of suitable additional components can be found in the other references which have been incorporated by reference in this application. Still further examples of such additional ingredients may be found in the *International Cosmetic Ingredient Dictionary and Handbook* ($9^{th}$ ed. 2002).

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 99% (such as from 0.01% to 90%) relative to the total weight of the composition and further such as from 0.1% to 50% (if present), including all ranges and subranges therebetween.

Needless to say, the composition of the invention should be cosmetically or dermatologically acceptable, i.e., it should contain a non-toxic physiologically acceptable medium and should be able to be applied to the eyelashes of human beings.

Non-limiting examples of such additional components include non-volatile oils such as silicone oils (for example, dimethicone, phenyl trimethicone, trimethyl pentaphenyl trisiloxane, etc) or hydrocarbon oils (for example, esters). In one embodiment of the present invention, the compositions of the present invention are substantially free of silicone oils (i.e., contain less than about 0.5% silicone oils). In another embodiment, the compositions are substantially free of non-silicone oils (i.e., contain less than about 0.5% non-silicone oils). In another embodiment, the compositions are substantially free of non-volatile oils (i.e., contain less than about 0.5% non-volatile oils).

According to preferred embodiments of the present invention, methods of treating, caring for and/or making up keratinous material such as skin, lips, hair and mucous membranes by applying compositions of the present invention to the keratinous material in an amount sufficient to treat, care for and/or make up the keratinous material are provided. Preferably, "making up" the keratin material includes applying at least one coloring agent to the keratin material in an amount sufficient to provide color to the keratin material.

According to other preferred embodiments, methods of covering or hiding defects associated with keratinous material such as imperfections or discolorations by applying compositions of the present invention to the keratinous material in an amount sufficient to cover or hide such defects are provided.

According to yet other preferred embodiments, methods of enhancing the appearance of keratinous material by applying compositions of the present invention to the keratinous material in an amount sufficient to enhance the appearance of the keratinous material are provided.

In accordance with the three preceding preferred embodiments, the compositions of the present invention comprising at least one polar modified polymer are applied topically to the desired area of the keratin material in an amount sufficient to treat, care for and/or make up the keratinous material, to cover or hide defects associated with keratinous material, skin imperfections or discolorations, or to enhance the appearance of keratinous material. The compositions may be applied to the desired area as needed, preferably once or twice daily, more preferably once daily and then preferably allowed to dry before subjecting to contact such as with clothing or other objects (for example, a glass or a topcoat). Preferably, the composition is allowed to dry for about 1 minute or less, more preferably for about 45 seconds or less. The composition is preferably applied to the desired area that is dry or has been dried prior to application, or to which a basecoat has been previously applied. Most preferably, the composition further comprises at least one coloring agent, at least one film forming agent, at least one viscosity increasing agent and/or at least one volatile oil.

According to a preferred embodiment of the present invention, compositions having improved cosmetic properties such as, for example, improved feel upon application (for example, texture, reduced drag or tackiness), increased anti-smudging properties, shine/color characteristics and/or increased long wear properties are provided.

According to further embodiments of the present invention, methods of improving the viscoelastic properties of a composition comprising adding at least one polar modified polymer to the composition are provided. In accordance with this embodiment, the at least one polar modified polymer is present in amounts sufficient to achieve the desired result.

According to other embodiments of the present invention, methods of improving the anti-smudging, transfer-resistance and/or long wear properties of a composition, comprising adding at least one polar modified polymer to the composition are provided. In accordance with this embodiment, the at least one polar modified is present in amounts sufficient to achieve the desired result.

According to further embodiments of the present invention, methods of improving the feel or texture of a composition, preferably a makeup compositions such as a foundation or lip composition, comprising adding at least one polar modified polymer to the composition are provided. In accordance with this embodiment, the at least one polar modified polymer is present in amounts sufficient to achieve the desired result.

According to yet other embodiments of the present invention, methods of making a composition comprising mixing together at least one other ingredient and at least one polar modified polymer to form a composition are provided. In particularly preferred embodiments, the polar modified polymer is in an aqueous phase, and the other ingredient is in an oil phase, and the other ingredient and the polar modified polymer are combined when the aqueous phase and the oil phase are combined. Such preferred procedures allow, among other things, the preparation of emulsions which can be substantially or essentially free of surfactants.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLES

Example 1&2

Foundation

|    | Trade name      | INCL Name                                      | EX1   | EX2   |
|----|-----------------|------------------------------------------------|-------|-------|
| A1 | DC-245          | Cyclopentasiloxane                             | 33.91 | 33.91 |
| A1 | PSPA            | NYLON-611/DIMETHICONE COPOLYMER                | 0.5   | 0.5   |
| A2 | KF-6028         | KF-6028                                        | 2.4   | 2.4   |
| A2 | Bentone         | DISTEARDIMONIUM HECTORITE                      | 0.94  | 0.94  |
| A2 | expancel 5551   | Acrylate Copolymer                             | 0.25  | 0.25  |
| A2 | KSG 710         | Dimethicone and Dimethicon/Polyglycerin        | 6     | 6     |
| B1 |                 | Pigment Grind                                  | 12    | 12    |
| C1 | Sunsphere H 51  | Silica                                         | 3     | 3     |
| C1 | Orgasol 2002    | Nylon 12                                       | 1     | 1     |
| D1 | Glycerin        | Glycerin                                       | 5     | 5     |
| D1 | Phenoxyethanol  | Phenoxyethanol                                 | 0.8   | 0.8   |
| D1 | CM401           | C26-C28 ALPHA OLEFIN MALEIC ACID ANHYDRIDE COPOLYMER | 14 | 8 |
| D1 | DI Water        | DI Water                                       | 17.7  | 23.7  |
| D1 |                 | Simethicone                                    | 0.1   | 0.1   |
| D1 | Amphisol k      | POTASSIUM CETYL PHOSPHATE                      | 2.4   | 2.4   |
|    |                 | Total                                          | 100   | 100   |

Example 1 was crumbly in form. Example 2 was mousse-like in form.

Example 3, 4 and 5

Long Wear and Transfer Resistance Foundations

|    | Trade Name      | INCI Name                                      | EX3  | EX4  | EX5  |
|----|-----------------|------------------------------------------------|------|------|------|
| A1 | isododecane     | Isododecane                                    | 35.6 | 35.6 | 35.6 |
| A1 | PP207           | Propylene-Ethylene-Maleic Anhydride Copolymer  | 0    | 4    | 0    |
|    | CM401           | C26-28 alpha olefin maleic acid anhydride wax  | 0    | 0    | 4    |
|    | PE400           | Polyethylene 400 Wax                           | 4    | 0    | 0    |
| A1 | regalite        | HYDROGENATED STYRENE/METHYL STYRENE/INDENE COPOLYMER | 10 | 10 | 10 |
| A2 | Bentone         | DISTEARDIMONIUM HECTORITE                      | 1.2  | 1.2  | 1.2  |
|    |                 | acrylate coplymer                              | 0.2  | 0.2  | 0.2  |
| A3 | KF-6028         | PEG-9 POLYDIMETHYLSILOXYETHYL DIMETHICONE (and) PEG-9 | 2.5 | 2.5 | 2.5 |
| A3 |                 | Pigment grind                                  | 11.5 | 11.5 | 11.5 |
| A3 | KSG 710         | Dimethicone and Dimethicone/Polyglycerin-3 Crosspolymer | 4 | 4 | 4 |
| A4 | ORGASOL 2002    | Nylon-12                                       | 1.5  | 1.5  | 1.5  |
|    | sodium choloride | sodium chloride                               | 1    | 1    | 1    |
|    | disodium edta   | disodium edta                                  | 0.2  | 0.2  | 0.2  |
| B  | Glycerin        | Glycerin                                       | 3    | 3    | 3    |
| B  | PHENONIP        | Phenoxyethanol etc.                            | 0.8  | 0.8  | 0.8  |
| B  | DI WATER        | DI WATER                                       | 24.5 | 24.5 | 24.5 |
|    |                 | total:                                         | 100  | 100  | 100  |

Example 3 did not contain a polar modified polymer. In contrast, examples 4 and 5 contained a polar modified polymer. Examples 4 and 5 possessed more transfer resistance and better (longer) wear properties than example 3.

Example 6

Washable Mascara (Emulsion)

| INCI Name | EX6 |
|---|---|
| Isododecane | 35.1 |
| Nylon-611/Dimethicone Copolymer | 1.5 |
| Iron Oxide | 6 |
| DI Water | 42 |
| Potassium Cetyl Phosphate | 2 |
| Methylparaben | 0.25 |
| Propylparaben | 0.05 |
| Propylene-Ethylene-Maleic Anhydride Copolymer (LicoCare PP 207 LP1332) | 12 |
| Phenoxyethanol (and) Methylparaben (and) Isopropylparaben (and) Isobutylparaben (and) Butylparaben | 1.1 |
| Total | 100 |

Example 7&8

Shiny and Long Wear Mascara

| INCI Name | EX7 | EX8 |
|---|---|---|
| Isododecane | 34.6 | 31.6 |
| Nylon-611/Dimethicone Copolymer | 3 | 3 |
| Iron Oxide | 6 | 6 |
| DI Water | 38 | 36 |
| Potassium Cetyl Phosphate | 2 | 2 |
| Propylene-Ethylene-Maleic Anhydride Copolymer (LicoCare PP 207 LP1332) | 10 | 10 |
| Polyvinylpyrrolidone | 5 | 10 |
| Methylparaben | 0.25 | 0.25 |
| Propylparaben | 0.05 | 0.05 |
| Phenoxyethanol (and) Methylparaben (and) Isopropylparaben (and) Isobutylparaben (and) Butylparaben | 1.1 | 1.1 |
| TOTAL | 100 | 100 |

Example 9, 10, 11&12

Lip Gloss

| | Trade Name | INCI Name | EX 9 | EX 10 | EX 11 | EX 12 |
|---|---|---|---|---|---|---|
| A | Kraton polymer G1657m | Polystyrene/Polyethylenebutylene/Polystyrene | 8.00 | 8.00 | 8.00 | 8.00 |
| | Regalite R1100 | hydrogenated styrene/methyl styrene/indiene | 16.00 | 16.00 | 16.00 | 16.00 |
| | polysylane lite | polyisobutene | 33.20 | 33.20 | 33.20 | 33.20 |
| B | Iso propyl palmitate | Iso propyl palmitate | 6.00 | 6.00 | 6.00 | 6.00 |
| | DC556 | phenyl trimethicone | 9.80 | 9.80 | 9.80 | 9.80 |
| | DC 555 | trimethyl pentaphenyl trisiloxane | 10.00 | 10.00 | 10.00 | 10.00 |
| | PURESYN6 | polydecene | 8.00 | 8.00 | 8.00 | 8.00 |
| | PURESYN150 | polydecene | 6.00 | 6.00 | 6.00 | 6.00 |
| C | fumed silica | fumed silica | 3.00 | 0.00 | 0.00 | 0.00 |
| | LicoCare PP 201 LP3332 | poly propylene wax | 0.00 | 3.00 | 0.00 | 0.00 |
| | LicoCare PP 203 LP3334 | poly propylene wax | 0.00 | 0.00 | 3.00 | 0.00 |
| | LicoCare PP 207 LP1332 | poly propylene-Maleic Anhydride wax | 0.00 | 0.00 | 0.00 | 3.00 |
| | | total= | 100.00 | 100.00 | 100.00 | 100.00 |

Example 9 contained fumed silica, and resulted in a composition which was not clear and which was very sticky (tacky) upon application. Examples 10 and 11 contained non-polar waxes, not polar modified polymers. These compositions were clear but tacky. Example 12, representative of the invention compositions, contained a polar modified polymer. Example 12 was both clear and non-tacky.

Example 13-18

Mascara

| Phase | INCI Name/Trade Name | EX 13 | EX 14 | EX 15 | EX 16 | EX 17 | EX 18 |
|---|---|---|---|---|---|---|---|
| A | DI Water | 62.28 | 64.28 | 58.28 | 48.28 | 53.28 | 54.28 |
| | Amphisol K | 1.73 | 1.73 | 1.73 | 1.73 | 1.73 | 1.73 |
| | PVP K90 | 2.00 | 0 | 0 | 10.00 | 5.00 | 10.00 |
| | Methylparaben | 0.25 | 0.25 | 0.25 | 0.25 | 0.25 | 0.25 |
| | Hydroxypropylcellulose | 0.20 | 0.20 | 0.20 | 0.20 | 0.20 | 0.20 |
| | Pentylene Glycol | 2.00 | 2.00 | 2.00 | 2.00 | 2.00 | 2.00 |
| | Di Sodium EDTA | 0.10 | 0.10 | 0.10 | 0.10 | 0.10 | 0.10 |
| | 50% Sodium Hydroxide | 0.50 | 0.50 | 0.50 | 0.50 | 0.50 | 0.5 |

-continued

| Phase | INCI Name/Trade Name | EX 13 | EX 14 | EX 15 | EX 16 | EX 17 | EX 18 |
|---|---|---|---|---|---|---|---|
| B1 | Steareth-2 | 2.10 | 2.10 | 2.10 | 2.10 | 2.10 | 2.10 |
|  | Steareth-20 | 4.44 | 4.44 | 4.44 | 4.44 | 4.44 | 4.44 |
|  | Cetyl Alcohol | 2.00 | 2.00 | 2.00 | 2.00 | 2.00 | 2.00 |
|  | Carnuaba Wax | 2.00 | 2.00 | 2.00 | 2.00 | 2.00 | 2.00 |
|  | Candellia Wax | 1.00 | 1.00 | 1.00 | 1.00 | 1.00 | 1.00 |
|  | Sunpuro Black | 5.00 | 5.00 | 5.00 | 5.00 | 5.00 | 5.00 |
|  | Rice Bran Wax | 3.00 | 3.00 | 3.00 | 3.00 | 3.00 | 3.00 |
|  | Propylparaben | 0.20 | 0.20 | 0.20 | 0.20 | 0.20 | 0.20 |
|  | Licocare PP207 LP3349 | 10.00 | 10.00 | 16.00 | 16.00 | 16.00 | 10.00 |
| C | Simethicone | 0.10 | 0.10 | 0.10 | 0.10 | 0.10 | 0.10 |
| E | Liquapar Optima | 1.10 | 1.10 | 1.10 | 1.10 | 1.10 | 1.10 |
|  | Total | 100.0 | 100.0 | 100.0 | 100.0 | 100.0 | 100.0 |

The effect on volumization of eyelashes which the different concentrations of polar modified polymer and liposoluble or dispersible rheological polymer in these examples have was measured. The different concentrations were added to the same base composition, as identified in examples 13-18. The compositions were then applied to eyelashes and the volumizing effect which the compositions had on the eyelashes were determined.

| Ingredient | Example 15 | Example 17 | Example 16 |
|---|---|---|---|
| PPMA | 16 | 16 | 16 |
| PVP K 90 | 0 | 5 | 10 |
| % volume increase | 130 | 257 | 338 |

| Ingredient | Example 14 | Example 13 | Example 18 |
|---|---|---|---|
| PPMA | 10 | 10 | 10 |
| PVP K 90 | 0 | 2 | 10 |
| % volume increase | 143 | 281 | 427 |

Example 19

Liquid Foundation

|  | Trade name | INCI Name | EX1 |
|---|---|---|---|
| A1 | DC-245 | Cyclopentasiloxane | 33.91 |
| A1 | PSPA | NYLON-611/DIMETHICONE COPOLYMER | 0.5 |
| A2 | KF-6028 | KF-6028 | 2.4 |
| A2 | Bentone | DISTEARDIMONIUM HECTORITE | 0.94 |
| A2 | expancel 5551 | Acrylate Copolymer | 0.25 |
| A2 | KSG 710 | Dimethicone and Dimethicon/Polyglycerin | 6 |
| B1 |  | Pigment Grind | 12 |
| C1 | Sunsphere H 51 | Silica | 3 |
| C1 | Orgasol 2002 | Nylon 12 | 1 |
| D1 | Glycerin | Glycerin | 5 |
| D1 | Phenoxyethanol | Phenoxyethanol | 0.8 |
| D1 | CM401 | C26-C28 ALPHA OLEFIN MALEIC ACID ANHYDRIDE COPOLYMER | 4 |
| D1 | DI Water | DI Water | 27.7 |
| D1 |  | Simethicone | 0.1 |
| D1 | Amphisol k | POTASSIUM CETYL PHOSPHATE | 2.4 |

The liquid foundation of example 19 was very creamy and easy to spread and blend. The foundation also provided a smooth and comfortable feeling upon application.

Examples 20, 21, and 22

Washable Mascaras (Emulsions)

| INCI Name | EX20 | EX21 | EX22 |
|---|---|---|---|
| Isododecane | 34.6 | 35.6 | 35.6 |
| Nylon-611/Dimethicone Copolymer | 6 | 0 | 3 |
| Beeswax | 3 | 0 | 0 |
| Carnauba Wax | 4 | 0 | 0 |
| Paraffin | 5 | 0 | 0 |
| Iron Oxide | 6 | 6 | 6 |
| DI Water | 38 | 40 | 40 |
| Potassium Cetyl Phosphate | 2 | 2 | 2 |
| Methylparaben | 0.25 | 0.25 | 0.25 |
| Propylparaben | 0.05 | 0.05 | 0.05 |
| Propylene-Ethylene-Maleic Anhydride Copolymer Licocare PP207 LP3349 | 0 | 15 | 12 |
| Phenoxyethanol (and) Methylparaben (and) Isopropylparaben (and) Isobutylparaben (and) Butylparaben | 1.1 | 1.1 | 1.1 |
|  | 100 | 100 | 100 |

Example 20 contained a polysilicone polyamide copolymer. Example 21 contained a polar modified polymer. Example 22 contained both a polysilicone polyamide copolymer and a polar modified polymer. Example 20 was unstable and grainy. Example 21 was stable but not creamy—it did not provide a smooth and comfortable feeling upon application. In contrast, Example 22 was both stable and creamy. Also, example 22 possessed excellent wear and smudging characteristics for 8 hours.

Example 23

Anhydrous Eyeliner

| Ingredient | Amount (% weight) |
|---|---|
| Isododecane | 70 |
| Nylon 611/dimethicone | 4 |
| Solids/Pigments | 6 |

-continued

| Ingredient | Amount (% weight) |
|---|---|
| Propylene-Ethylene-Maleic Anhydride Copolymer Licocare PP207 LP3349 | 20 |

Lipstick Compositions

Inventive Examples 24-26

| | Ex. 24 | Ex. 25 | Ex. 26 |
|---|---|---|---|
| Polypropylsilsesquioxane (and) Pentamethylheptane | 28.04 | 26.70 | 26.70 |
| Polar modified polymer LICOCARE CM 401 LP 3345 | 2.80 | 2.67 | 2.67 |
| Isododecane | 38.11 | 35.37 | 35.37 |
| Polyethylene Wax PE400 | 18.69 | 11.76 | 11.76 |
| Synthetic Wax PERFORMA V 260 | 0.00 | 11.76 | 0.00 |
| Synthetic Wax PERFORMA V 103 | 0.00 | 0.00 | 11.76 |
| Yellow 6 Lake | 3.19 | 3.03 | 3.03 |
| Blue 1 Lake | 0.20 | 0.19 | 0.19 |
| Red 7 | 0.67 | 0.63 | 0.63 |
| Titanium Dioxide | 3.38 | 3.22 | 3.22 |
| Iron Oxides | 0.31 | 0.29 | 0.29 |
| Mica | 2.14 | 2.03 | 2.03 |
| Mica (and) Titanium Dioxide (and) Iron Oxides | 2.47 | 2.35 | 2.35 |
| TOTAL | 100.00 | 100.00 | 100.00 |
| Wear | 81.7 ± 5.2 | 80.0 ± 4.5 | |
| Transfer after 5 minutes | 2.0 ± 0.8 | 2.0 ± 0.8 | |
| Immediate Shine | 45 ± 11.4 | 38 ± 21.6 | |
| Shine at 1 hr. | 42 ± 16.0 | 40 ± 21.3 | |
| Shearing | 125.45 | 99.35 | |
| crumble upon slice test | N | Y | |
| Application | dry | dry | |
| Stickiness (1: very sticky 5: not sticky) | 4 | 5 | |

Example 27

Four non-transfer lipsticks were prepared as Compositions A-D below. Of these compositions, only Composition B contained polar metallocene wax. Compositions C and D contained both silicone resin (T resin) and Regalite. Composition A contained only silicone resin (T resin). The ingredients of compositions A-D are set forth below.

| Ingredient | Composition A | Composition B | Composition C | Composition D |
|---|---|---|---|---|
| T resin | 30 | 22.27 | 15 | 4.97 |
| Regalite | | | 15 | 34.76 |
| POLAR METALLOCENE WAX | | 2.27 | | |
| ISODODECANE | 45 | 52.68 | 45 | 35.43 |
| POLYETHYLENE | 15 | 15.14 | 15 | 14.9 |
| YELLOW 6 LAKE | 2.58 | 1.95 | 2.58 | 2.56 |
| BLUE 1 LAKE | 0.16 | 0.12 | 0.16 | 0.16 |
| RED 7 | 0.54 | 0.41 | 0.54 | 0.54 |
| TITANIUM DIOXIDE | 2.74 | 2.07 | 2.74 | 2.72 |
| IRON OXIDES | 0.25 | 0.19 | 0.25 | 0.25 |
| MICA | 3.73 | 1.31 | 3.73 | 1.72 |
| MICA (and) TITANIUM DIOXIDE (and) IRON OXIDES | | 1.51 | | 1.99 |
| FRAGRANCE | | 0.08 | | |

Wear properties of all four compositions were determined. It was determined that composition B containing both polar metallocene wax and silicone resin possessed the best wear characteristics, the best transfer-resistance characteristics, and the best feel (non-sticky) characteristics of all the compositions. The data reflecting these improved properties of composition B are set forth below.

| Wear Score | Composition A | Composition B | Composition C | Composition D |
|---|---|---|---|---|
| % wear after classic wear test (goal: >65) | 75.8 (+/−9.2) | 81.7 (+/−5.2) | 69.2 (+/−16.3) | 65.8 (+/−9.2) |
| transfer 5 mins (NA) | 3.0 (+/−1.0) | 1.5 (+/−0.5) | 3.0 (+/−0.5) | 2.0 (+/−1.0) |
| immediate shine (goal >100) | 30 (+/−7.8) | 47 (+/−15.7) | 43 (+/−9.3) | 68 (+/−20.5) |
| 1 hr shine | 37 (+/−10.2) | 40 (+/−12.8) | 35 (+/−16.8) | 38 (+/−15.7) |
| Shearing | 62.3 | 75 | 40.2 | 88.15 |
| crumble upon slice test (Y:N) | N | N | N | N |
| Application | smooth | Dry | smooth | smooth |
| Stickiness (1: very sticky 5: not sticky) | 1 | 4 | 1 | 1 |
| overtime driness on lip (1: very dry 5: comfortable) | 2 | 1 | 2 | 3 |

-continued

| | Ex. 24 | Ex. 25 | Ex. 26 |
|---|---|---|---|
| overtime dryness on lip (1: very dry 5: comfortable) | 1 | 2 | |

What is claimed is:

1. A composition comprising at least one oil-soluble polar modified polymer compromising at least one C2-C4 monomer and modified with at least one hydrophilic unit, and having a weight-average molecular weight of less than or equal to 25 000 g/mol and a melting point above 75° C.; and
   at least one polysilicone-polyamide copolymer.

2. The composition of claim 1, wherein the composition is an emulsion.

3. The composition of claim 1, wherein the composition is anhydrous.

4. The composition of claim 1, further comprising at least one coloring agent.

5. The composition of claim 1, wherein the polysilicone-polyamide copolymer is a nylon 611/dimethicone copolymer.

6. The composition of claim 1, wherein the at least one oil-soluble polar modified polymer consists essentially of polypropylene and maleic anhydride units.

7. A method of making up skin comprising applying the composition of claim 1 to the skin.

8. A method of making up lips comprising applying the composition of claim 1 to the lips.

9. A method of making up eyelashes comprising applying the composition of claim 1 to the eyelashes.

10. The composition of claim 1, wherein the composition further comprises at least one oil-soluble high carbon polar modified polymer comprising at least one C26-C28 monomer and modified with at least one hydrophilic unit, and having a weight-average molecular weight of less than or equal to 30000 g/mol and a crystallinity of 8% to 60%.

11. The composition of claim 10, wherein the polysilicone-polyamide copolymer is a nylon 611/dimethicone copolymer.

12. The composition of claim 10, wherein the at least one high carbon polar modified polymer consists essentially of C26-C28 alpha olefin and maleic acid anhydride units.

13. The composition of claim 1, wherein the at least one oil-soluble polar modified polymer is a polypropylene and/or polyethylene maleic anhydride wax.

14. The composition of claim 13, in the form of a mascara.

15. The composition of claim 6, wherein the polysilicone-polyamide copolymer is a nylon 611/dimethicone copolymer.

16. The composition of claim 13, wherein the polysilicone-polyamide copolymer is a nylon 611/dimethicone copolymer.

* * * * *